(12) United States Patent
Woodward

(10) Patent No.: US 10,972,644 B2
(45) Date of Patent: Apr. 6, 2021

(54) WEARABLE RING FOR HOLDING CAMERA

(71) Applicant: Harley Woodward, Trinity (JE)

(72) Inventor: Harley Woodward, Trinity (JE)

( * ) Notice: Subject to any disclaimer, the term of this patent is extended or adjusted under 35 U.S.C. 154(b) by 94 days.

(21) Appl. No.: 16/379,035

(22) Filed: Apr. 9, 2019

(65) Prior Publication Data

US 2020/0329184 A1 Oct. 15, 2020

(51) Int. Cl.
*H04N 5/225* (2006.01)
*A61F 5/41* (2006.01)
*H04N 7/18* (2006.01)

(52) U.S. Cl.
CPC ............. *H04N 5/2257* (2013.01); *A61F 5/41* (2013.01); *H04N 7/185* (2013.01); *A61F 2005/414* (2013.01)

(58) Field of Classification Search
CPC ........ H04N 5/2257; H04N 7/185; A61F 5/41; A61F 2005/414
See application file for complete search history.

(56) References Cited

U.S. PATENT DOCUMENTS

2015/0318885 A1* 11/2015 Earle ................... H04B 1/3888
455/575.6

* cited by examiner

*Primary Examiner* — Yogesh K Aggarwal
(74) *Attorney, Agent, or Firm* — Inventa Capital PLC

(57) ABSTRACT

A wearable device, such as a ring, is used to be worn on at least one part of a human body. A wearable device includes a body having a bottom surface and a top surface, an opening defined between the top surface and the bottom surface. The opening is used to receive therethrough and hold the at least one part of the human body, such as a finger or a penis. A pocket is defined in the body between the opening and the top surface for holding the camera presenting an activation button to turn on and turn off the camera. The body includes a slot defined in the top surface of the body and extending to the pocket to receive the activation button extending through the slot as the camera is disposed in the pocket to turn off or turn on the camera as the body is worn on the penis or the finger.

9 Claims, 12 Drawing Sheets

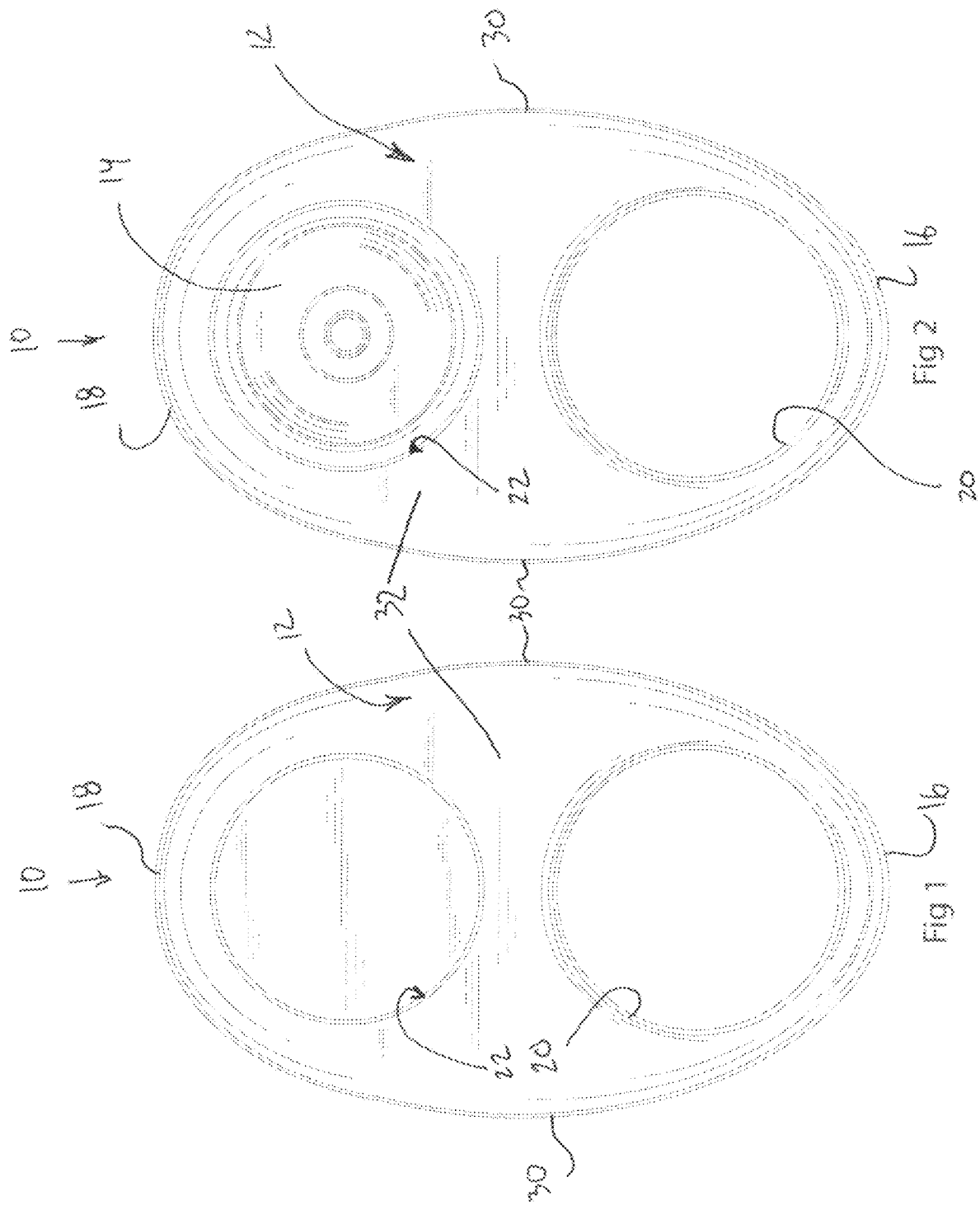

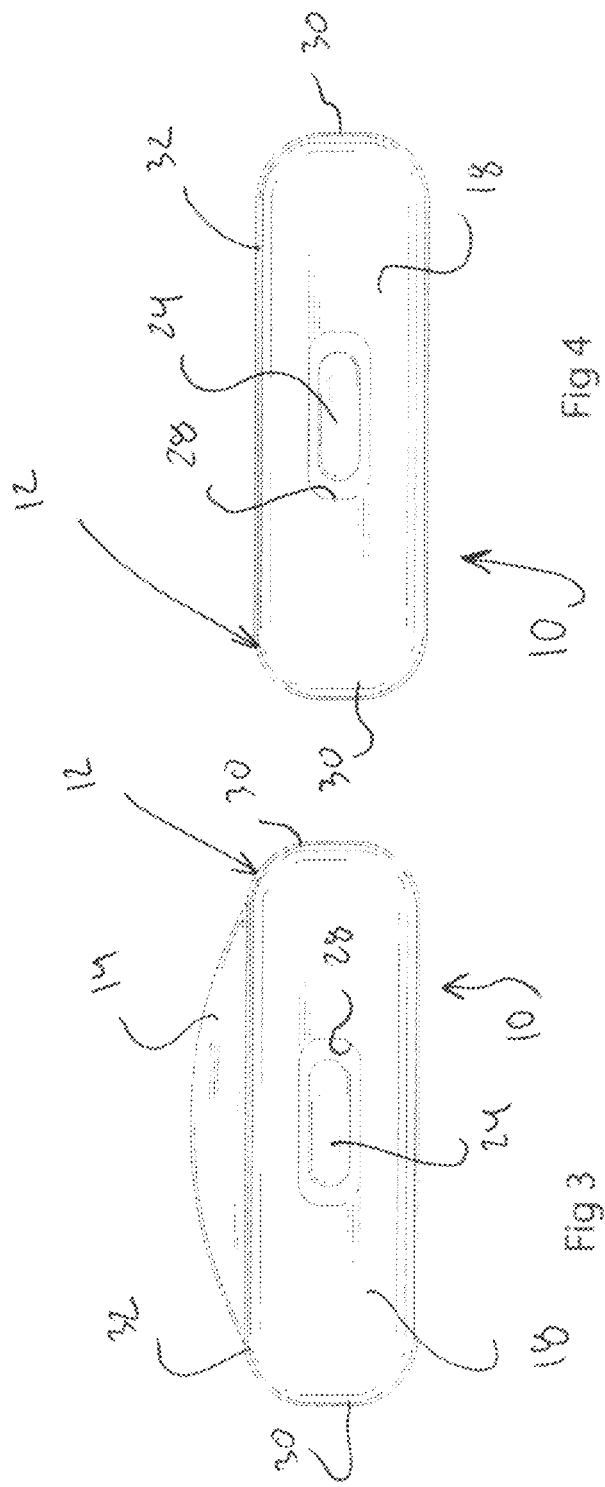

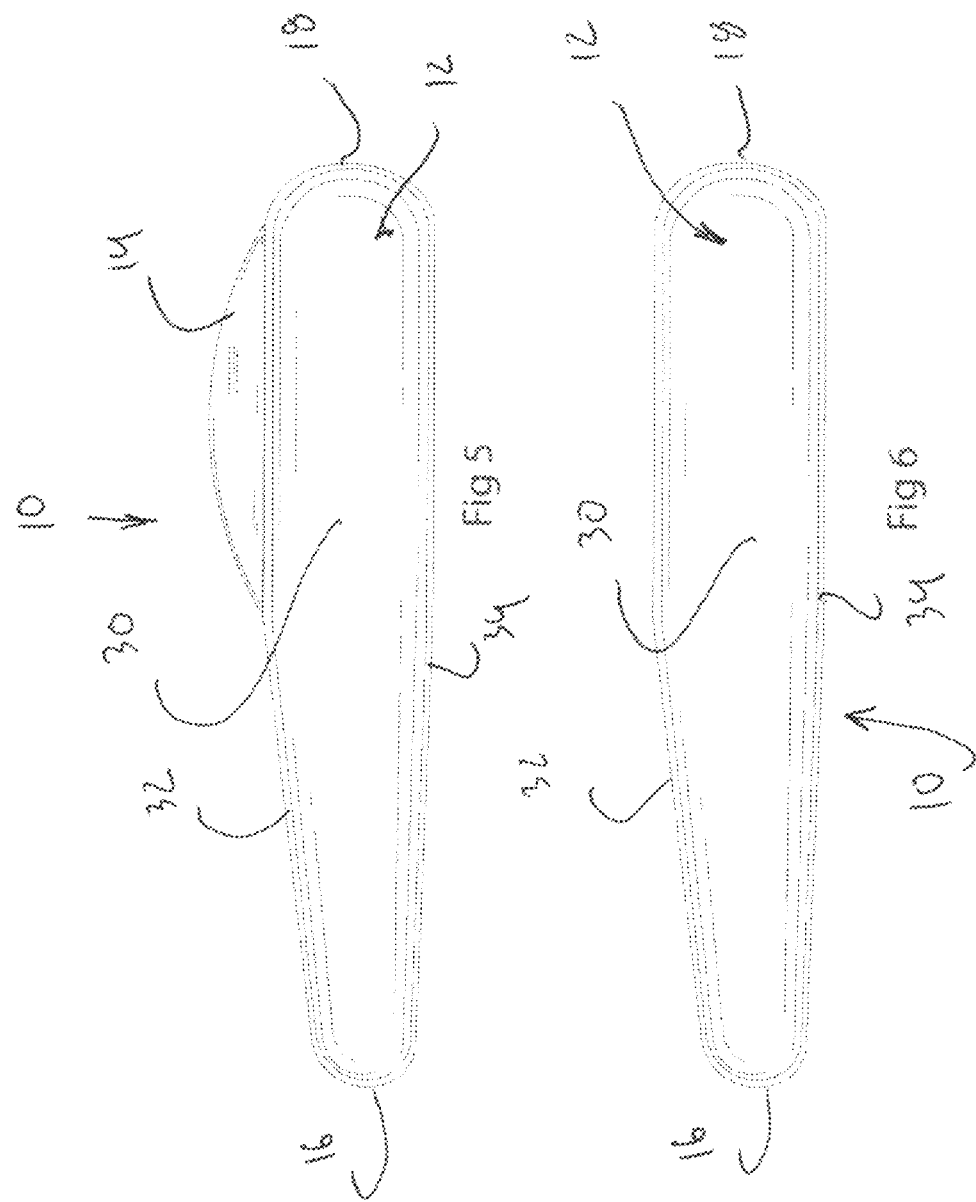

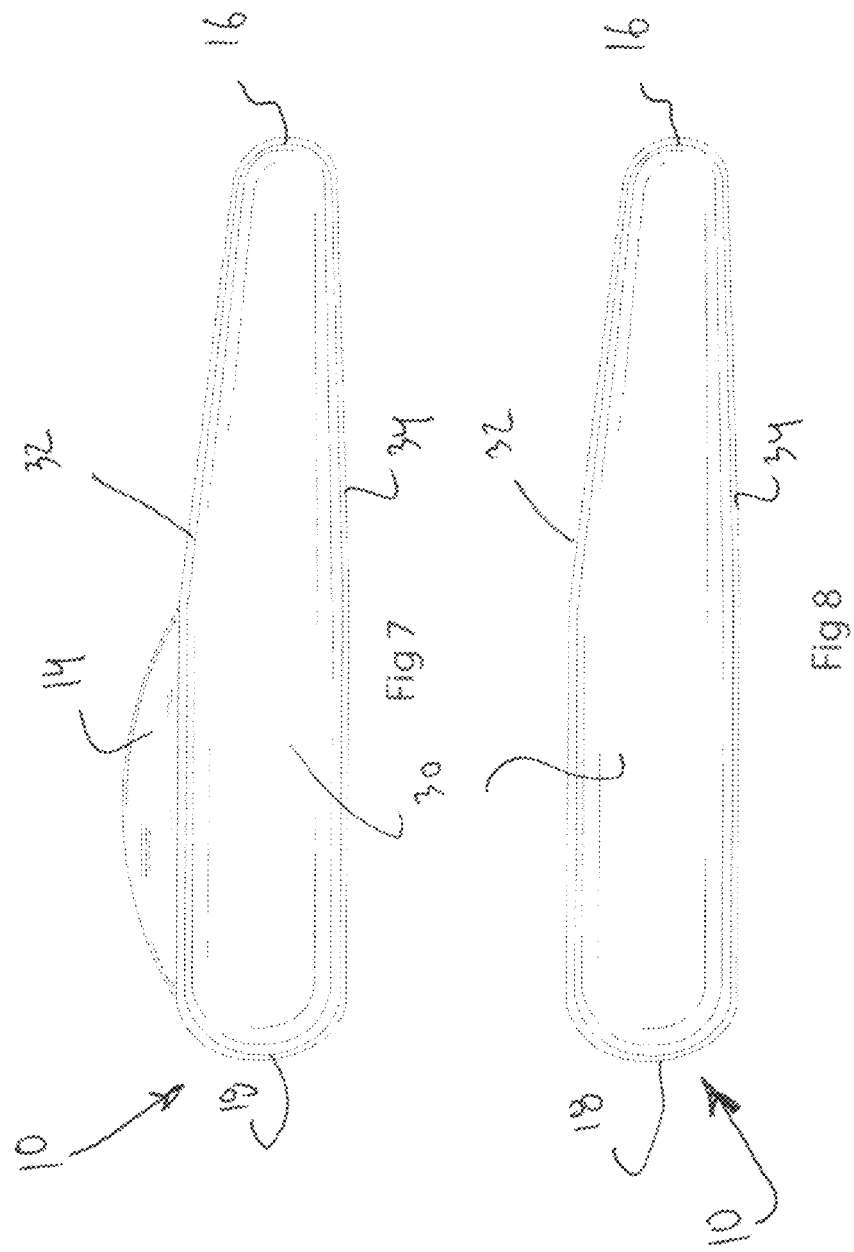

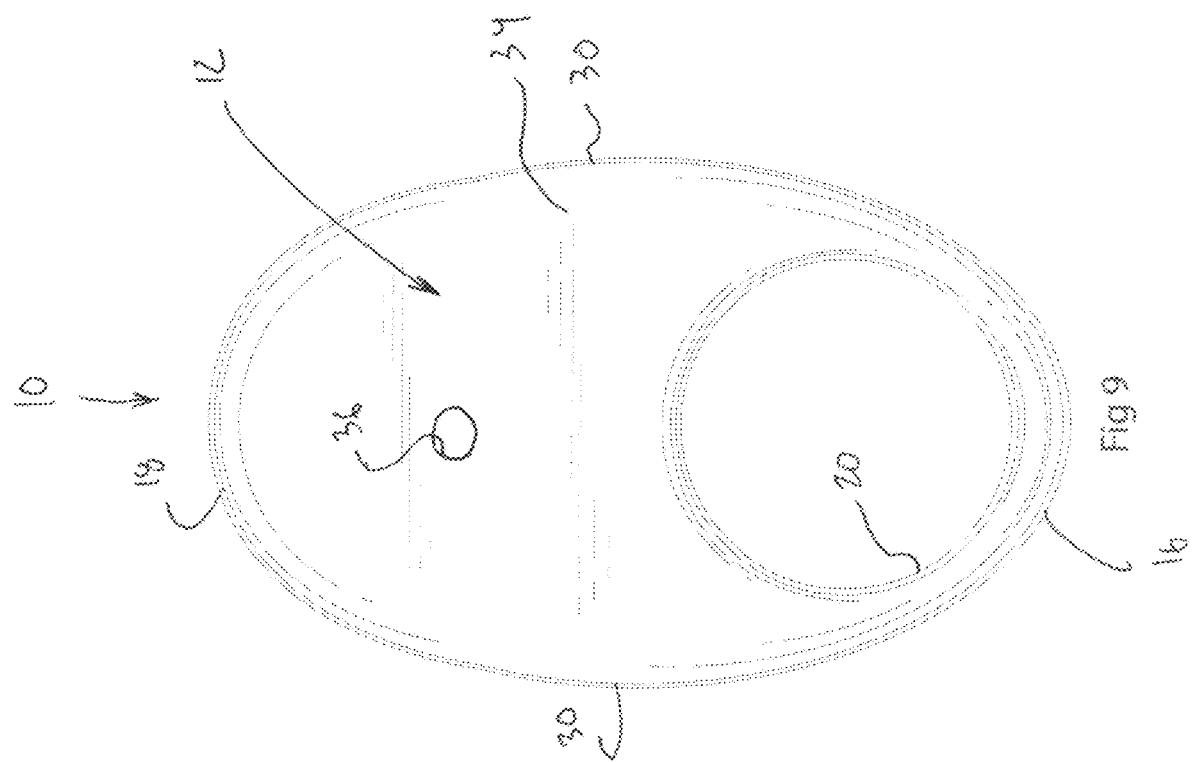

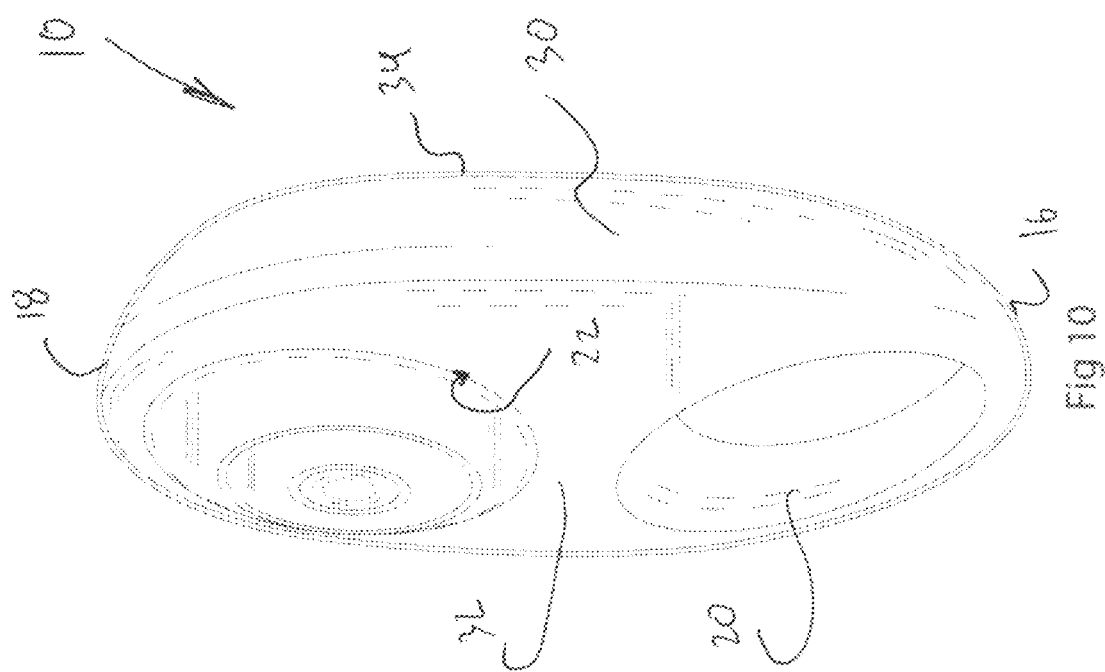

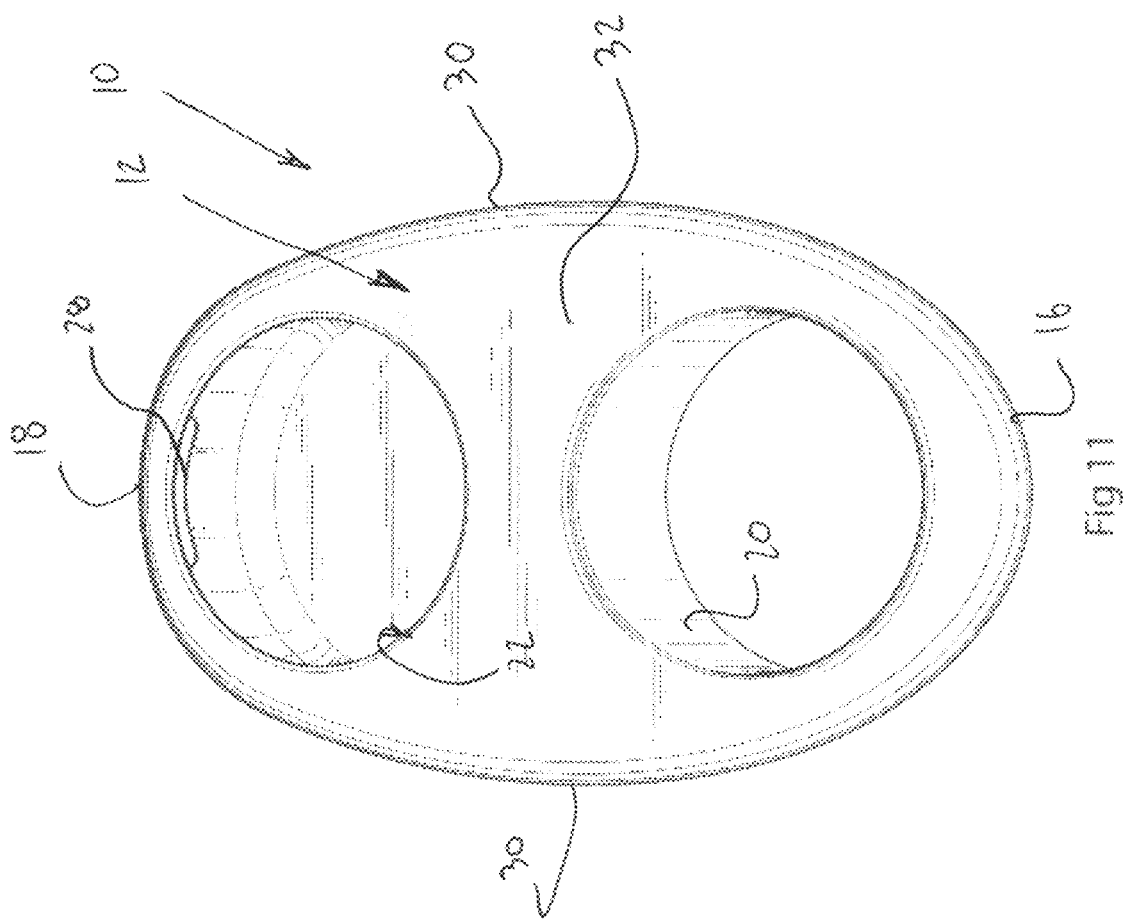

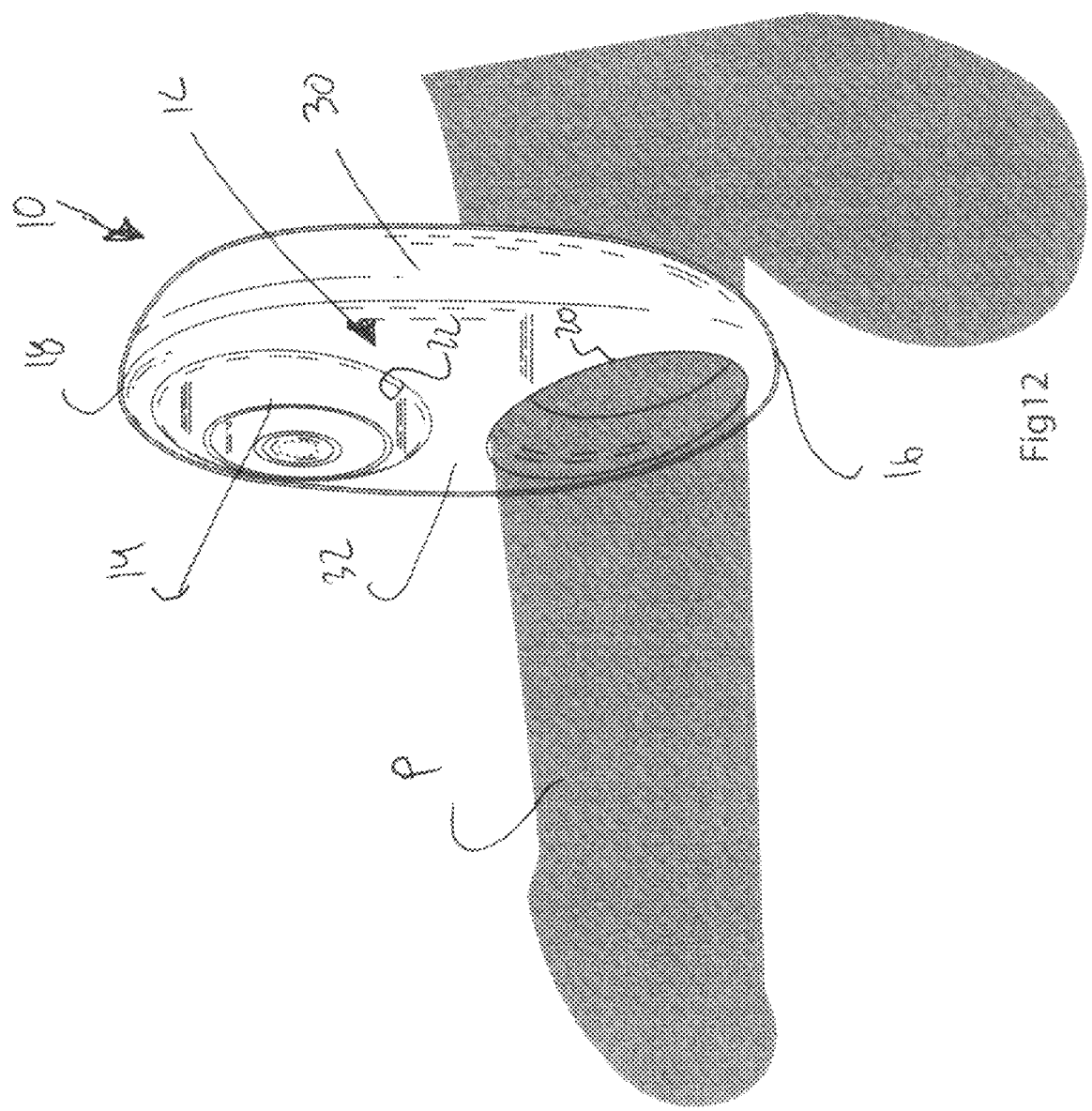

WEARABLE RING FOR HOLDING CAMERA

FIELD OF THE INVENTION

The present invention relates to the field of sex toys, in particular to a penis erection support ring that assists a penile function when mounted on a penis of a male during sexual intercourse.

BRIEF DESCRIPTION OF THE INVENTION

Various sex toys have been around since the beginning of recorded history. Common older types of penetrative sex toys include: dildos, Ben Wa balls, horseshoes, double penetration dildos, strap-on dildos, kegel exercisers, motorized sex machines, butt-plugs, anal beads, and prostate massagers; any of which can be fitted with vibrators. These sex toys are traditionally made of silicon, rubber, hard plastic, metal, glass, or cyber skin; although stranger materials can and are used.

One of the most popular sex toys is a cock ring. The cock ring is a ring worn around the penis, usually at the base. The primary purpose of wearing the cock ring is to restrict the flow of blood from the erect penis in order to produce a stronger erection or to maintain an erection for a longer period of time. When used in cases of erectile dysfunction (ED), they are known by various other names, such as erection rings and tension rings. The cock ring may be used for medical purposes. A man may wear an erection ring because he has erectile dysfunction (ED). When used for ED, a purpose-designed vacuum pump is used to produce an erection by simple mechanical and hydrodynamical action in spite of vascular or nerve damage, and the ring is slid off the pump's cylinder onto the base of the penis to maintain the erection before it is lost. The cock ring is also used for recreational purposes. The cock ring may be used during sex or masturbation to prolong or enhance erections, delay orgasm, or for the sensation of tightness and engorgement that wearing one produces; vibrating models apply vibration to the base of the user's penis and to their partner.

To the extent as being effective, there is always a need for new and improved systems, devices, and methods that can improve and prolong sexual pleasure and add new excitement to sexual live of partners. The present invention aims to solve this problem by simple and convenient means.

SUMMARY OF THE INVENTION

A wearable device, such as a ring, includes a body used to be worn on at least one part of a human body. A wearable device includes a body having a bottom surface and a top surface, an opening defined between the top surface and the bottom surface. The opening is used to receive therethrough and hold the at least one part of the human body, such as a finger or a penis. A pocket is defined in the body between the opening and the top surface for holding the camera presenting an activation button to turn on and turn off the camera. The body includes a slot defined in the top surface of the body and extending to the pocket to receive the activation button extending through the slot as the camera is disposed in the pocket to turn off or turn on the camera as the body is worn on the penis or the finger.

An advantage of the present invention is to provide an innovative cock ring designed as a silicone ring housing that is wearable on a penis or dildo.

Another advantage of the present invention is to provide the innovative cock ring, which is made in a way that it houses a WiFi compatible camera which is controlled, viewed via a mobile application.

Still another advantage of the present invention is to provide the innovative cock ring used for sexual stimulation as well as recording intimate moments at a completely new angle/POV.

The objects and advantages of the present invention will be more readily apparent from inspection of the following specification, taken in connection with the accompanying drawing, wherein like numerals refer to like parts throughout and in which an embodiment of the present invention is described and illustrated.

The exact manner in which the foregoing and other objects and advantages of the invention are achieved in practice will become more clearly apparent when reference is made to the following detailed description of the preferred embodiments of the invention described in detail in the following specification and shown in the accompanying drawings, where in like reference numbers indicate corresponding parts throughout.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a front side view of a wearable ring for holding a camera;

FIG. 2 is a front view of the wearable ring for holding the camera with the camera thereinside;

FIG. 3 is a top view of the wearable ring for holding the camera with the camera inside;

FIG. 4 is a top view of the wearable ring for holding the camera;

FIG. 5 is a right side view of the wearable ring for holding the camera with the camera inside;

FIG. 6 is a right side view of the wearable ring for holding the camera;

FIG. 7 is a left side view of the wearable ring for holding the camera with the camera inside;

FIG. 8 is a left side view of the wearable ring for holding the camera;

FIG. 9 is a rear side view of the wearable ring for holding the camera;

FIG. 10 is a perspective view of the wearable ring for holding the camera;

FIG. 11 is a perspective view of the wearable ring for holding the camera taken from the bottom;

FIG. 12 is a perspective side view of the wearable ring for holding the camera positioned on a part of a human body;

DETAILED DESCRIPTION OF THE INVENTION

Figure 13:
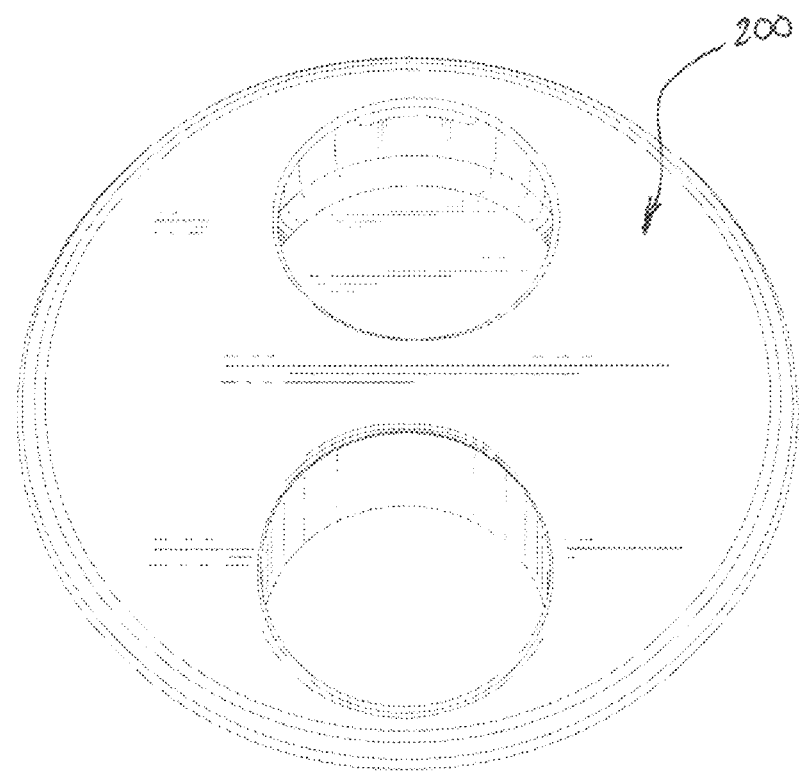
FIG. 13 is another perspective view of the wearable ring for holding the camera.

FIG. 1 through 12, illustrates a wearable device, such as a ring, generally shown at 10. The device 10 is designed as a silicone ring housing or a body, generally indicated at 12, which is wearable on a penis or dildo P, it is made in a way that it houses a WiFi compatible camera 14, which is controlled, viewed via a mobile application. The device 10 is used for sexual stimulation as well as recording intimate moments at a completely new angle and point of view.

As used herein, the singular forms "a," "an," and "the" include plural referents unless the context clearly dictates otherwise. Furthermore, as used herein, the term "based on" includes based at least in part on. Thus, a feature that is described as based on some cause, can be based only on that cause, or based on that cause and on one or more other causes.

It will be apparent that multiple embodiments of this disclosure may be practiced without some or all of these specific details. In other instances, well-known process operations have not been described in detail in order not to unnecessarily obscure the present embodiments. The following description of embodiments includes references to the accompanying drawing. The drawing shows illustrations in accordance with example embodiments. These example embodiments, which are also referred to herein as "examples," are described in enough detail to enable those skilled in the art to practice the present subject matter. The embodiments can be combined, other embodiments can be utilized, or structural, logical and operational changes can be made without departing from the scope of what is claimed. The following detailed description is, therefore, not to be taken in a limiting sense, and the scope is defined by the appended claims and their equivalents.

Alluding to the above, for purposes of this patent document, the terms "or" and "and" shall mean "and/or" unless stated otherwise or clearly intended otherwise by the context of their use. The term "a" shall mean "one or more" unless stated otherwise or where the use of "one or more" is clearly inappropriate. The terms "comprise," "comprising," "include," and "including" are interchangeable and not intended to be limiting. For example, the term "including" shall be interpreted to mean "including, but not limited to."

FIG. 1 through 12, the wearable device 10 includes the body 12 used to be worn on at least one part of a human body, such as the penis P. The body 12 includes a bottom surface 16 and a top surface 18. An opening 20 is defined between the top surface 18 and the bottom surface 16. The opening 20 is used to receive therethrough and hold the at least one part of the human body, such as a finger or the penis P.

The body 12 includes a pocket, generally indicated at 22, is defined in the body 12 between the opening 20 and the top surface 18 for holding the camera 14 presenting an activation button 24 to turn on and turn off the camera 14. The body 12 includes a slot 28 defined in the top surface 18 of the body 12 and extending to the pocket 22 to receive the activation button 24 extending through the slot 28 as the camera 14 is disposed in the pocket 22 to turn off or turn on the camera 14 as the body 12 is worn on the penis P or the finger.

Figure 14:
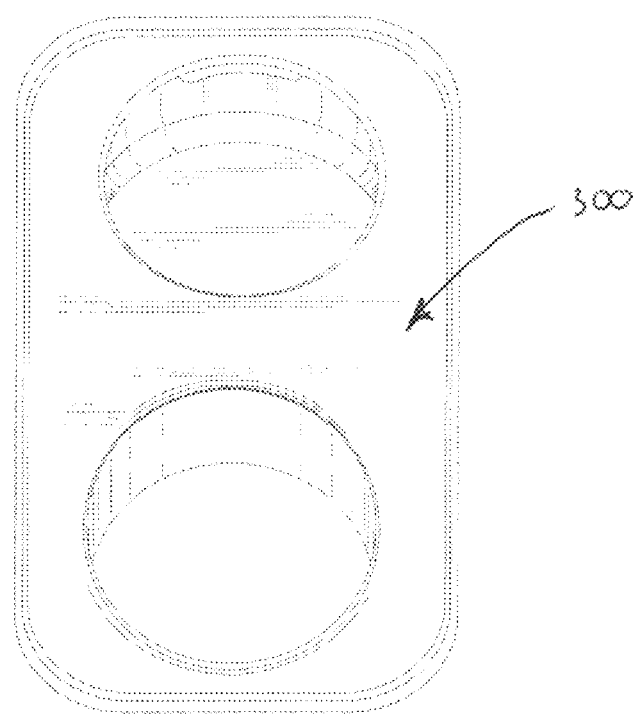
FIG. 14 is still another perspective view of the wearable ring for holding the camera.

Alluding to the above, the body 12 includes a side surface 30, a front surface 32 presenting a concave configuration and a rear surface 34 presenting a flat configuration. The body 12 is formed from a silicone material allowable to resiliently change forms of the body 12 to apply pressure to the penis P to hold erection and flex the body 12 to easily place in and remove out the camera 14. As shown in FIGS. 9 and 14, the body 12 may also include a second slot 36 defined in the rear surface 34 and a third slot 38 defined in the side surface 30 in case if other camera 14 may be used where an activation button may be located on the rear side or on the side wall of the camera 14.

Figure 15:
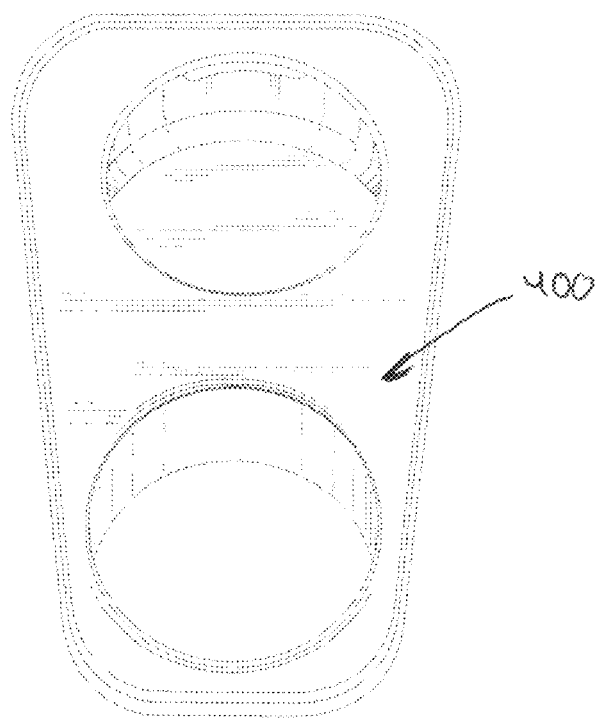
FIG. 15 is still another perspective view of the wearable ring for holding the camera.
Figure 16:
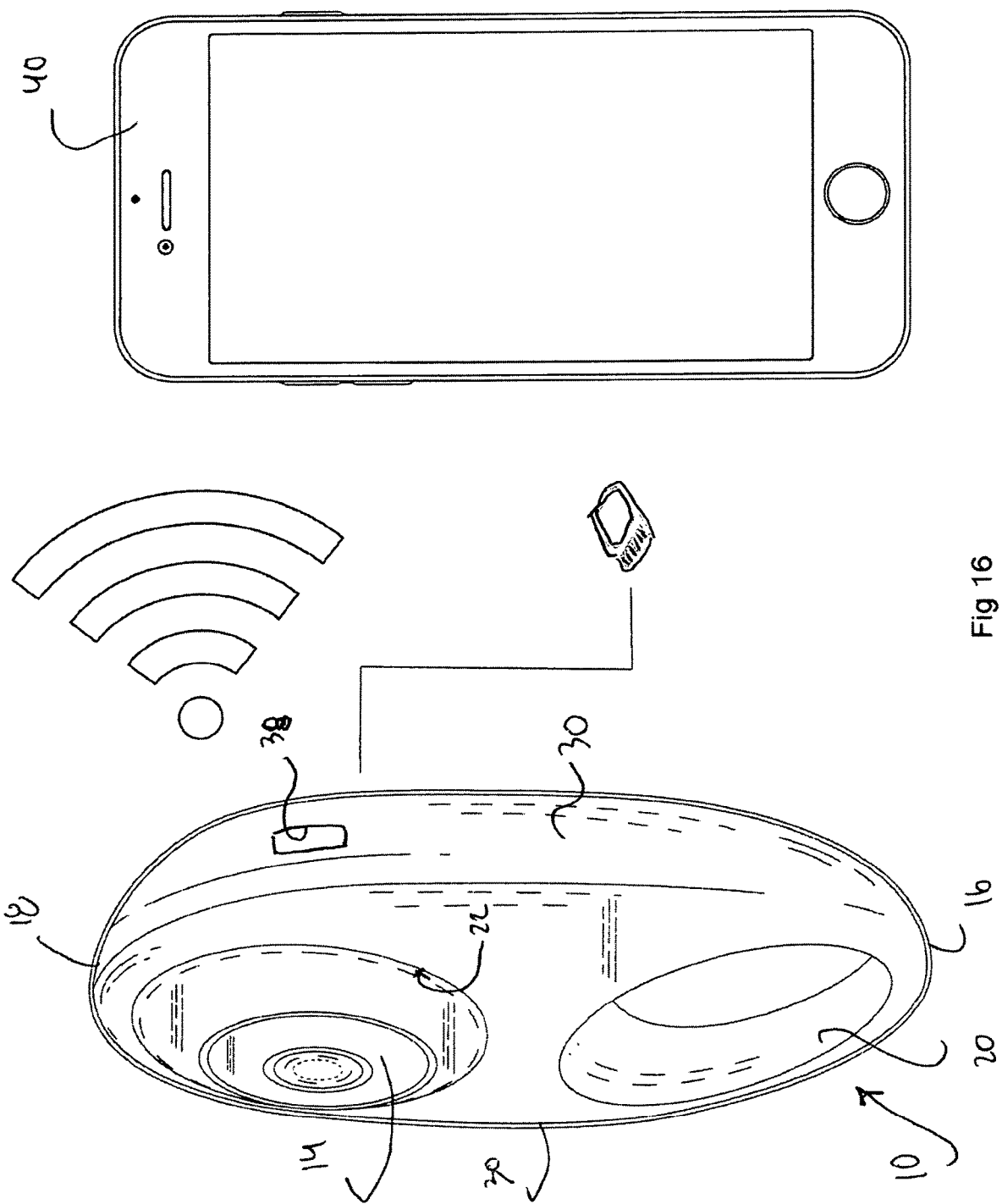
FIG. 16 illustrated schematic view of the wearable ring for holding the camera operably communicated with a device such as a mobile phone.

The body 12 may be formed from other materials besides the silicone. The body 12 includes an oval configuration as shown in FIGS. 1 and 16, for example, wherein the camera 14 is a WiFi compatible camera, is wirelessly communicated with a personal computing device such as a personal computer and a mobile phone 40, so partners engaging in erotic relationship, can view the sexual act and enjoy the pleasure. There are numerous alternative embodiments of the body 12. For example, FIG. 13, shows the body 200 having a circular configuration, FIG. 14 shows the body 300 having a rectangular configuration, and FIG. 15, includes yet another embodiment where the body 400 presents a conical configuration. Other embodiments may be available and the ones shown in the aforementioned Figures are not intended to limit the scope of the present invention.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A wearable device for a camera, said wearable device is used to be worn on at least one part of a human body, said wearable device comprising:

a body having a bottom surface and a top surface, said body presenting an opening defined between said top surface and said bottom surface, said opening is used to receive therethrough and hold the at least one part of the human body;

a pocket defined in said body between said opening and said top surface for holding the camera presenting an activation button to turn on and turn off the camera, said pocket presenting a circular configuration; and said body presenting a slot defined in said top surface of said body and extending to said pocket to receive the activation button extending through said slot as the camera is disposed in said pocket to turn off or turn on the camera as said body is worn on the at least one part of the human body, said body including a front surface and a rear surface with said front surface being concave and said rear surface being flat.

2. The wearable device of claim 1, wherein said body is formed from a silicone material allowable to resiliently change forms of said body.

3. The wearable device of claim 2, wherein said body presents an oval configuration.

4. The wearable device of claim 3, wherein said body includes a side surface extending between and interconnecting said top surface and said bottom surface.

5. The wearable device of claim 1, wherein the camera is a WiFi compatible camera wirelessly communicated with a personal computing device such as a personal computer and a mobile phone.

6. The wearable device of claim 1, wherein said body presents a circular configuration.

7. The wearable device of claim 1, wherein said body presents a rectangular configuration.

8. The wearable device of claim 1, wherein said body presents a triangular configuration.

9. A wearable device for a camera, said wearable device is used to be worn on at least one part of a human body, said wearable device comprising:
- a body having a bottom surface and a top surface, a side surface, a front surface presenting a concave configuration and rear surface presenting a flat configuration, said body formed from a silicone material allowable to resiliently change forms of said body;
- said body presenting an opening defined between said top surface and said bottom surface, said opening is used to receive therethrough and hold the at least one part of the human body;
- a pocket defined in said body between said opening and said top surface for holding the camera presenting an activation button to turn on and turn off the camera, said pocket presenting a circular configuration;
- said body presenting a slot defined in said top surface of said body and extending to said pocket to receive the activation button extending through said slot as the camera is disposed in said pocket to turn off or turn on the camera as said body is worn on the at least one part of the human body; and
- said body presents an oval configuration, wherein the camera is a WiFi compatible camera wirelessly communicated with a personal computing device such as a personal computer and a mobile phone.

\* \* \* \* \*